US007687666B2

(12) United States Patent
Chan et al.

(10) Patent No.: US 7,687,666 B2
(45) Date of Patent: Mar. 30, 2010

(54) METHODS FOR PREPARING SULFONAMIDE SUBSTITUTED ALCOHOLS AND INTERMEDIATES THEREOF

(75) Inventors: Anita Wai-Yin Chan, Fort Lee, NJ (US); Jianxin Ren, Nanuet, NY (US); Mousumi Ghosh, Elmwood Park, NJ (US); Arkadiy Rubezhov, West Nyack, NY (US); Panolil Raveendranath, Monroe, NY (US); Joseph Zeldis, New City, NY (US)

(73) Assignee: Wyeth, Madison, NJ (US)

( * ) Notice: Subject to any disclaimer, the term of this patent is extended or adjusted under 35 U.S.C. 154(b) by 36 days.

(21) Appl. No.: 11/706,636

(22) Filed: Feb. 15, 2007

(65) Prior Publication Data

US 2007/0197830 A1 Aug. 23, 2007

Related U.S. Application Data

(60) Provisional application No. 60/774,453, filed on Feb. 17, 2006.

(51) Int. Cl.
*C07C 209/78* (2006.01)
*C07C 303/12* (2006.01)
*C07C 29/147* (2006.01)

(52) U.S. Cl. .......................... 564/468; 564/79; 568/884

(58) Field of Classification Search ........................ None
See application file for complete search history.

(56) References Cited

U.S. PATENT DOCUMENTS

| 3,143,542 | A * | 8/1964 | Schneider et al. ........... 540/450 |
| 5,795,890 | A | 8/1998 | Nakae et al. |
| 5,962,231 | A | 10/1999 | Yue et al. |
| 6,362,178 | B1 | 3/2002 | Niewohner et al. |
| 6,476,029 | B1 | 11/2002 | Niewohner et al. |
| 6,610,734 | B2 | 8/2003 | Kreft et al. |
| 6,657,070 | B2 | 12/2003 | Resnick |
| 6,667,342 | B1 | 12/2003 | Clarke et al. |
| 6,683,081 | B2 | 1/2004 | Niewohner et al. |
| 6,800,764 | B2 | 10/2004 | Kreft et al. |
| 6,803,365 | B2 | 10/2004 | Niewohner et al. |
| 6,878,742 | B2 | 4/2005 | Kreft et al. |
| 7,166,622 | B2 | 1/2007 | Kreft et al. |
| 2003/0013892 | A1 | 1/2003 | Resnick |
| 2003/0229127 | A1* | 12/2003 | Kreft et al. .................. 514/369 |
| 2004/0006050 | A1 | 1/2004 | Kreft et al. |
| 2004/0063737 | A1 | 4/2004 | Lucking et al. |
| 2004/0198778 | A1 | 10/2004 | Kreft et al. |
| 2005/0171180 | A1 | 8/2005 | Resnick et al. |
| 2007/0037778 | A1 | 2/2007 | Kreft et al. |

FOREIGN PATENT DOCUMENTS

| EP | 769498 | 4/1997 |
| JP | 09241262 | 9/1997 |
| JP | 11343279 | 12/1999 |
| WO | WO-03-063797 | 8/2003 |
| WO | WO-03/076437 | 9/2003 |
| WO | WO-03/088908 | 10/2003 |
| WO | WO-03/103660 | 12/2003 |
| WO | WO-2004/078731 | 9/2004 |
| WO | WO-2004/092155 | 10/2004 |

OTHER PUBLICATIONS

Aversa et al., "L-Cysteine, a Versatile Source of Sulfenic Acids. Synthesis of Enantiopure Alliin Analogues", J. Org. Chem., 70(6):1986-1992 (Mar. 18, 2005).
Dondoni et al., "Design and Use of an Oxazolidine Silyl Enol Ether as a New Homoalanine Carbanion Equivalent for the Synthesis of Carbon-Linked Isosteres of O-Glycosyl Serine and N-Glycosyl Asparagine", J. Org. Chem., 64(3):933-944 (Feb. 5, 1999).
Sham et al., "Renin Inhibitors. Design and Synthesis of a New Class of Conformationally Restricted Analogs of Angiotensinogen", J. Med. Chem., 31(2):284-295 (Feb. 1988).
Berry et al., "A Convenient Method for the Preparation of Enantiomerically Pure 2-Substituted N-Tosylaziridines", Synlett., 1:41-44 (Jan. 1992).
Bowman et al., "A Facile Method for the N-Alkylation of α-Amino Esters", Tet. 53(46):15787-15798 (Nov. 17, 1997).
Chataigner et al., "Discovery of a New Efficient Chiral Ligand for Copper-Catalyzed Enantioselective Michael Additions by High-Throughput Screening of a Parallel Library", Ang. Chem. Int. Ed., 39(5):916-918 (Mar. 3, 2000).
Cintrat et al., "Preparation of Chiral 2-Stannyloxazolidines and First Considerations on the Transacetalisation Reaction Mechanism", Eur. J. Org. Chem, 20:4251-4267 (Oct. 2004).
Egboh et al., "Synthesis and Characterization of Some Polyurethane lonomers", Polymer, 23(8):1167-1171 (Jul. 1982).
Gandon et al., "Tris(trimethylsilyl)silane: An Unprecedented Enhancement in the Diastereoselectivity of Radical Cyclisations to Give 2,4-Disbstituted Piperidines", Org. & Biomolec. Chem. 2(16):2270-2271 (2004; Epub date Jul. 19, 2004).
Ghosh et al., "Chelation-controlled Ester-Derived Titanium Enolate Aldol reaction: Diastereoselective syn-aldols with mono- and Bidentate Aldehydes", Tet. Lett., 43(32):5621-5624 (Aug. 5, 2002).
Fuji et al., "Ring Opening of Optically Active CIS-Disubstituted Aziridino Alcohols: An Enantiodivergent Synthesis of Functionalized Amino Alcohol Derivatives", Heterocycles, 42(2):701-722 (1996).
Hedley et al., "Development of a [3+3] Cycloaddition Strategy Toward Functionalized Piperidines", J. Org. Chem., 68(11):4286-4292 (Jan. 3, 2003: Epub date Apr. 22, 2003).
Hudlicky et al., "JOC Additions and Corrections", J. Org. Chem, 68(2):674 (2003: Epub date Jan. 1, 2003).

(Continued)

*Primary Examiner*—Brian J Davis
(74) *Attorney, Agent, or Firm*—Scott K. Larsen; Howson & Howson LLP

(57) ABSTRACT

Processes for preparing amino alcohols or salts thereof and sulfonamide substituted alcohol compounds are provided. Desirably, the sulfonamide substituted alcohol compounds are heterocyclic sulfonamide trifluoroalkyl-substituted alcohol compounds or phenyl sulfonamide trifluoroalkyl-substituted alcohol compounds.

31 Claims, No Drawings

OTHER PUBLICATIONS

Hudlicky et al., "Total Synthesis and Biological Evaluation of Amaryllidaceae Alkaloids: Narciclasine, ent-7-Deoxypancratistatin, Regioisomer of 7-Deoxypancratistatin, 10b-epi-Deoxypancratistatin, and Truncated Derivatives", J. Org. Chem., 67(25):8726-8743 (2002: Epub date Jul. 26, 2002).

Ibuka et al., "Aza-Payne Rearrangement of Activated 2-Aziridinemethanols and 2,3-Epoxy Amines Under Basic Conditions", J. Org. Chem., 60(7):2044-2058 (1995).

Ibuka et al., "Unprecedented Rearrangement Reaction of 2-Aziridinemethanols with "Lower Order" Lithium Methylcyanocuprate", Tet. Lett., 34(46):7421-7424 (Nov. 12, 1993).

Ibuka et al., "A Thermodynamic Preference of Chiral N-Methanesulfonyl and N-Arenesulfonyl 2,3-cis-3-Alkyl-2-Vinylaziridines over Their 2,3-Trans-Isomers: Useful Palladium(0)-Catalyzed Equilibration Reactions for the Synthesis of (E)-Alkene Dipeptide Isosteres", J. Org. Chem., 62(4):999-1015 (1997).

Moran et al., "A Concise Asymmetric Route to Nuphar Alkaloids. A Formal Synthesis of (-)-Deoxynupharidine", Org. Lett., 5(19):3427-3429 (Jun. 23, 2003: Epub date Aug. 28, 2003).

Ohno et al., "A 2,3-Cis-Selective Synthesis of Aziridines Bearing a Vinyl Group from Allyl Methyl Carbonates and Allyl Mesylates", J. Chem. Soc, Perkin Trans. 1, 22:3703-3716 (1998).

Ohno et al., "Stereodivergent Synthesis of Chiral 2-Alkenylaziridines: Palladium(0)-Catalyzed 2,3-cis-Selctive Aziridination and Base-Mediated 2,3-trans-Selective Aziridination", Chem. & Pharm. Bull., 52(1):111-119 (Jan. 2004).

Ohno et al., "Palladium(0)-Catalyzed Stereoselective Cyclization of Allenenes: Divergent Synthesis of Pyrrolidines and 3-Azabicyclo[3.1.0]Hexanes from Single Allenenes", J. Org. Chem., 69(13):4541-4544 (2004: Epub date May 28, 2004).

Otsuka et al., "Catalytic Asymmetric Reduction of Acetophenone Using Optically Active N-Sulfonyloxazaborolidine as a Catalyst", Memoirs of the Faculty of Science, Kyushu Univ., Series C: Chemistry 19(1):23-28 (1993).

Su et al., "Stereochemical Diversity Through Cyclodimerization: Synthesis of Polyketide-like Macrodiolides", Org. Lett., 5(12):2149-2152 (2003: Epub date May 15, 2003).

Tanner et al., "Studies of Regio- and Stereoselectivity in Some Nucleophilic Ring Opening Reactions of N-Tosyl-3-Phenyl-2-Aziridinemethanols and Derivatives", Tet. 51(30):8279-8288 (Jul. 24, 1995).

Tanner et al., "Regioselective Nucleophilic Ring Opening of 2,3-Aziridino Alcohols", Tet. 48(29):6069-6078 (1992).

Takahashi et al., "Synthesis and Absolute Configuration of Optically Pure 4-Isopropyl-N-Tosyl-1,3-Oxazolidines", Heterocycles 33(1):281-290 (1992).

Wanner et al., "A Dual Metathesis Route to Oligomeric Sulfonamides", Tet. Left., 43(6):917-921 (Feb. 4, 2002).

Atsushi, "3-Oxa-2,7-diazabicyclo(3.3.0)octane Derivative", English abstract of Japanese Patent No. 09-241262 (Sep. 16, 1997).

Shionogi & Co Ltd., "Sulfonamide Derivatives are TNF-α Inhibitors", English abstract of Japanese Patent No. 11-343279 (Dec. 14, 1999).

Chemical Diversity Research Institute, "Quinoline-Carboxylic Acids and the Derivatives Thereof, A Focused Library", English abstract of International Patent Publication No. WO-2004/078731.

Tanner et al., "Enanoselective Routes toward 1β-Methylcarbapenems from Chiral Aziridines", Tetrahedron, 48(29):6079-6086, (1992).

Otsuka et al., "Borane O-Adduct can be an intermediate in Chiral N-Sulfonyloxazaborolidine-Catalyzed Enantioselective Reduction of Ketones", SYNLETT, (May 1995).

Abiko et al., "New isoxazolidine-based chiral auxiliaries for asymmetric syntheses", Tetrahedron Letters, 38(18):3261-3264 (1997).

Reddy et al., "A practical protocol for chemoselective N-methylation of vicinal amino alcohols", Tetrahedron Letters, 41:949-951 (2000).

Altava et al., "A general route for the preparation of polymer-supported N-tosyl aminoalcohols and their use as chiral auxiliaries", Tetrahedron Letters, 42:1673-1675 (2001).

Brüggeman et al., "Stereoselective formation of quaternary carbon centres with chiral 3- sulfonyl-1,3-oxazolidines and titanium enolates", Tetrahedron, 58:321-340 (2002).

Bartels et al., "Asymmetric Ir[1]-Catalysed Allylic Alkylation of monosubstituted allylic acetates with phosphorus amidites as ligands", Eur. J. Org. Chem., 1097-1103 (2003).

Ohno et al., "Synthesis of Allenes from Allylic alcohol derivatives bearing a bromine atom using a palladium(0)/Diethylzinc system", J. Org. Chem., 67(4):1359-1367 (Feb. 22, 2002).

Office Action dated Apr. 20, 2009 issued in corresponding European Patent Application No. 07705892.7.

Response to Office Action dated Oct. 30, 2009 filed in corresponding European Patent Application No. 07705892.7.

* cited by examiner

METHODS FOR PREPARING SULFONAMIDE SUBSTITUTED ALCOHOLS AND INTERMEDIATES THEREOF

CROSS-REFERENCE TO RELATED APPLICATIONS

This application claims the benefit of the priority of U.S. Provisional Patent Application No. 60/774,453, filed Feb. 17, 2006.

BACKGROUND OF THE INVENTION

This invention relates to inhibitors of beta amyloid production, which have utility in the treatment of Alzheimer's disease.

Alzheimer's Disease (AD) is the most common form of dementia (loss of memory) in the elderly. The main pathological lesions of AD found in the brain consist of extracellular deposits of beta amyloid protein in the form of plaques and angiopathy and intracellular neurofibrillary tangles of aggregated hyperphosphorylated tau protein. Recent evidence has revealed that elevated beta amyloid levels in the brain not only precede tau pathology but also correlate with cognitive decline. Further suggesting a causative role for beta amyloid in AD, recent studies have shown that aggregated beta amyloid is toxic to neurons in cell culture.

Heterocyclic- and phenyl-sulfonamide compounds, specifically fluoro- and trifluoroalkyl-containing heterocyclic sulfonamide compounds, have been shown to be useful for inhibiting β-amyloid production.

What is needed in the art are alternate processes for preparing sulfonamide compounds, which are useful for inhibiting β-amyloid production, and the intermediates thereof.

SUMMARY OF THE INVENTION

In one aspect, methods for preparing amino alcohols or salts thereof are provided.

In another aspect, methods for preparing sulfonamide substituted alcohols are provided.

Other aspects and advantages of the invention will be readily apparent from the following detailed description of the invention.

DETAILED DESCRIPTION OF THE INVENTION

The methods describe herein provide routes to sulfonamide substituted alcohols. The methods also provide novel steps for preparing the intermediates thereof, including amino alcohols.

A. Methods of Preparing Amino Alcohols

A method for preparing an amino alcohol, or salt thereof, from an aminoester is described. See, Scheme 1, wherein $R^1$, $R^2$, $R^3$ and $R^4$ are defined below.

Scheme 1

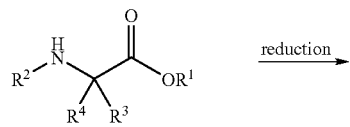

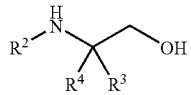

In one embodiment, the amino alcohol is of the structure:

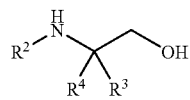

wherein, $R^2$ is a protecting group; $R^3$ is selected from among hydrogen, lower alkyl and substituted lower alkyl; $R^4$ is selected from among $(CF_3)_n$alkyl, $(CF_3)_n$(substituted alkyl), $(CF_3)_n$alkylphenyl, $(CF_3)_n$alkyl(substituted phenyl), and $(F)_n$cycloalkyl; and n is 1 to 3. Desirably, $R^2$ is 1-methylbenzyl.

The term "protecting group" as used herein refers to a group that protects an amino functional group. Desirably, the protecting group may be removed by deprotection under conditions known to those of skill in the art. A variety of protecting groups are known in the art and include those set forth in Green et al., "Protective Groups in Organic Synthesis", 3rd Edition, John Wiley & Sons Inc, June, 1999 and US Patent Publication No. 2004/0198778, which is hereby incorporated by reference herein. In one embodiment, the protecting group is a chiral protecting group. In another embodiment, the protecting group is an optionally substituted alkyl, cycloalkyl, or carbonyl. In a further embodiment, the protecting group is 1-methylbenzyl, benzyl, t-butyloxycarbonyl (BOC), or acetyl, among others. In yet another embodiment, the protecting group is 1-methylbenzyl.

In a further embodiment, the amino alcohol is of the following structure:

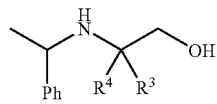

wherein, $R^3$ is selected from among hydrogen, lower alkyl and substituted lower alkyl; $R^4$ is selected from among $(CF_3)_n$alkyl, $(CF_3)_n$(substituted alkyl), $(CF_3)_n$alkylphenyl, $(CF_3)_n$alkyl(substituted phenyl), and $(F)_n$cycloalkyl; and n is 1 to 3.

In one example, $R^4$ is $(CF_3)_n$alkyl such as $CF_3CH_2$, $CH(CH_3)CH_2CF_3$, $CH(CH_2CF_3)_2$, $CH(CH_3)CF_3$, or $CH(CF_3)_2$. In another example, $R^4$ is $(F)_n$cycloalkyl, desirably $(F)_2$cycloalkyl, more desirably $(F)_2$cyclohexane and bicyclo[3.1.0]hexane, and most desirably 4,4-difluoro-cyclohexane and 4,4-difluorobicyclo[3.1.0]-3-hexane.

In one embodiment, the amino alcohol is:

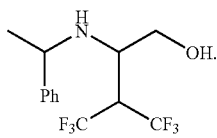

In a further embodiment, the amino alcohol is (2S)-4,4,4-trifluoro-2-{[(1R)-1-phenylethyl]amino}-3-(trifluoromethyl)butan-1-ol:

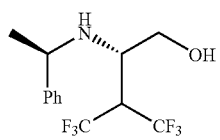

Alternatively, an amino alcohol salt of the following structure can be prepared from the aminoesters noted above.

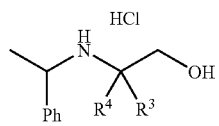

wherein, $R^3$ is selected from among hydrogen, lower alkyl and substituted lower alkyl; $R^4$ is selected from among $(CF_3)_n$alkyl, $(CF_3)_n$(substituted alkyl), $(CF_3)_n$alkylphenyl, $(CF_3)_n$alkyl(substituted phenyl), and $(F)_n$cycloalkyl; and n is 1 to 3.

In another embodiment, the amino alcohol salt is:

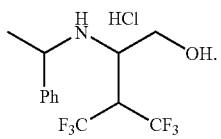

In a further embodiment, the amino alcohol salt is:

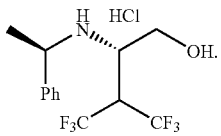

The amino alcohols are prepared by reducing the aminoester. The reduction is performed by adding the aminoester to a reducing agent. The term "reducing agent" as used herein refers to a compound or complex that converts the ester functional group of the aminoester to an alcohol functional group. One of skill in the art would readily be able to select a suitable reducing agent for the reduction. Suitable reducing agents include hydride reducing agents including, without limitation, sodium borohydride ($NaBH_4$), lithium aluminum hydride (LAH), lithium borohydride, diisobutylaluminum hydride (DIBAL-H), sodium bis-methoxy ethoxy aluminum hydride, sodium bis(2-methoxyethoxy)aluminum hydride (red-Al), k-selectride, among others, including those set forth in "Comprehensive Organic Transformations", R. C. Larock, VCH Publishers, Inc., New York, N.Y., 1989, which is hereby incorporated by reference herein. Desirably, the reducing agent is DIBAL-H.

The reduction is typically performed using a non-reactive solvent. The term "non-reactive solvent" as used herein refers to a solvent that does not react with any of the reagents utilized during the reduction. Desirably, the non-reactive solvent utilized during the reduction includes toluene, tetrahydrofuran (THF), hexanes, heptane, dichloromethane, cyclohexane, among others.

The inventors have found that when the aminoester is added to the reducing agent, i.e., DIBAL-H, the yield of amino alcohol is higher than if the reducing agent is added to the aminoester. Typically, the amino alcohol is prepared in a yield of greater than about 90%, greater than about 91%, greater than about 92%, greater than about 93%, greater than about 94%, or greater than about 95%. In one embodiment, the amino alcohol is prepared in a yield of about 90 to about 95%.

The temperature utilized during the reduction is higher than about −60° C. In one embodiment, the reduction to the amino alcohol is performed at about −60° to about −10° C. In another embodiment, the reduction is performed at about −20 to about −10° C. In a further embodiment, the reduction is performed at about −8 to −11° C. In yet another embodiment, the reduction is performed at about −10° C.

The reduction to the amino alcohol is later quenched using a protic solvent. By the term "protic solvent" is meant a solvent that contains a hydrogen source ($H^+$) that can be released in a solution. Typically, the hydrogen source is attached to an oxygen atom of the protic solvent. In one embodiment, the protic solvent contains a hydroxyl group. In another embodiment, the protic solvent is an alcohol, such as ethanol. In a further embodiment, the protic solvent is a protic acid. The term "protic acid" as used herein includes, without limitation, strong and weak acids such as hydrochloric acid, sulfuric acid, phosphoric acid, acetic acid, trihaloacetic acid, hydrogen bromide, maleic acids, sulfonic acids, propionic acids, tartaric acids, lactic acids, camphoric acids, aspartic acids, citronellic acids, $BCl_3$, ethanolic acids, hydrogen sulfide, methanesulfonic acid, trifluoroacetic acid, among others. In yet another embodiment, the protic solvent is a mixture of solvents that contain hydrogen atoms that can be released in solution.

A number of aminoesters can be reduced and can be determined by one of skill in the art utilizing techniques and knowledge in the art and in the instant specification. Desirably, the aminoester contains one or more chiral carbon centers. More desirably, the aminoester is a protected aminoester. Most desirably, the aminoester is an N-protected aminoester. In one embodiment, the aminoester is of the following structure:

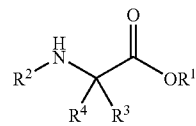

wherein, $R^1$ is alkyl or benzyl; $R^2$ is a protecting group; $R^3$ is selected from among hydrogen, lower alkyl and substituted lower alkyl; $R^4$ is selected from among $(CF_3)_n$alkyl, $(CF_3)_n$(substituted alkyl), $(CF_3)_n$alkylphenyl, $(CF_3)_n$alkyl(substituted phenyl), and $(F)_n$cycloalkyl; and n is 1 to 3.

In another embodiment, the aminoester is of the following structure, wherein $R^1$, $R^3$, and $R^4$ are defined above:

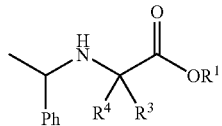

In a further embodiment, the aminoester is of the following structure, wherein $R^1$, $R^3$, and $R^4$ are defined above:

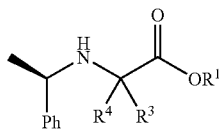

In still another embodiment, the aminoester is:

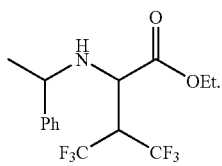

In yet a further embodiment, the aminoester is:

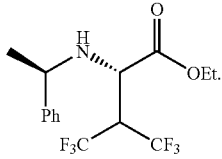

In one example, a method is provided for preparing an amino alcohol, or salt thereof, from an aminoester including reducing the aminoester by adding the aminoester to diisobutylaluminum hydride at about −60° to about −10° C.

In another example, a method is provided for preparing an amino alcohol of the structure:

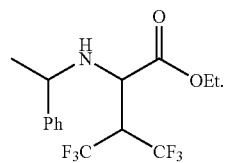

wherein, an aminoester of the following structure is reduced by adding the aminoester to diisobutylaluminum hydride at about −60° to about −10° C.

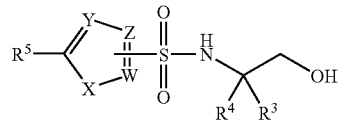

B. Methods for Preparing Sulfonamide Substituted Alcohols

Also provided are methods for preparing sulfonamide substituted alcohols. In one embodiment, the sulfonamide substituted alcohol is substituted with one or more trifluoroalkyl groups. In another embodiment, the sulfonamide substituted alcohol is a heterocyclic sulfonamide substituted alcohol or phenylsulfonamide substituted alcohol. See, Scheme 2.

In one embodiment, the sulfonamide substituted alcohol is of the structure:

wherein, $R^3$ is selected from among H, lower alkyl and substituted lower alkyl; $R^4$ is selected from among $(CF_3)_n$alkyl, $(CF_3)_n$(substituted alkyl), $(CF_3)_n$alkyl phenyl, $(CF_3)_n$alkyl (substituted phenyl), and $(F)_n$cycloalkyl; n is 1 to 3; $R^5$ is selected from among H, halogen, $CF_3$, diene fused to Y when Y is C, and substituted diene fused to Y when Y is C; W, Y and Z are independently selected from among C, $CR^6$ and N, wherein at least one of W, Y or Z is C; X is selected from among O, S, $SO_2$, and $NR^7$; $R^6$ is selected from among H, halogen, $C_1$ to $C_6$ alkyl, and substituted $C_1$ to $C_6$ alkyl; and $R^7$ is selected from among H, $C_1$ to $C_6$ alkyl, and $C_3$ to $C_8$ cycloalkyl.

Scheme 2

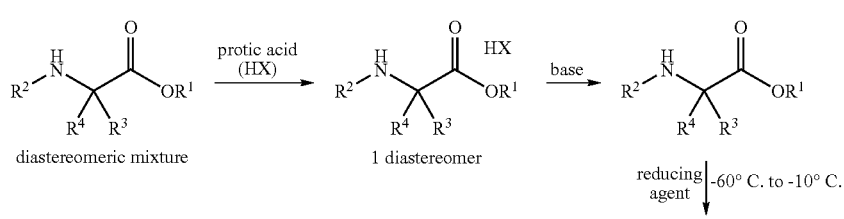

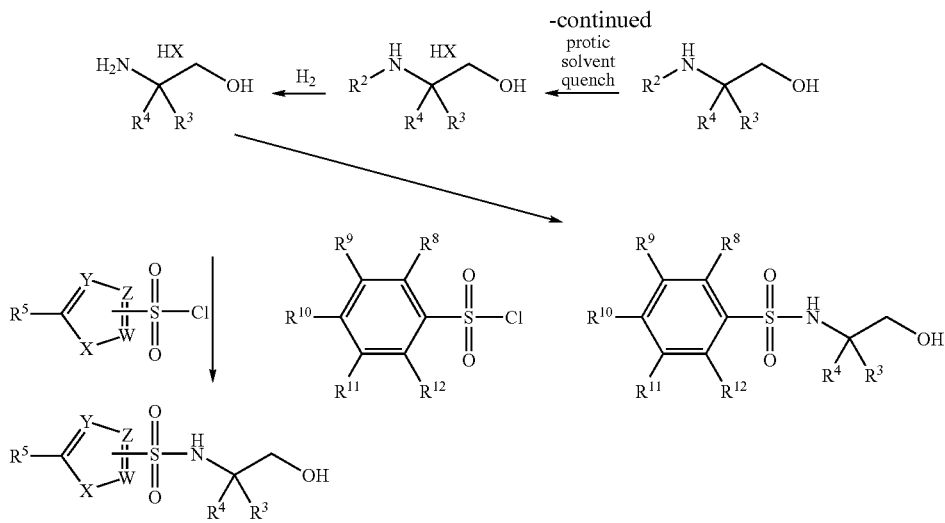

The point of attachment of the W-X-Y-Z-C heterocyclic ring to the $SO_2$ group is not a limitation. The ring may be attached to the $SO_2$ group through a carbon-atom or nitrogen-atom.

In one embodiment, the compounds prepared as described herein are thiophenesulfonamides, more desirably 5-halo thiophenesulfonamides, and most desirably 5-halo thiophene sulfonamides with β-branches in the side chain of a primary alcohol.

In a further embodiment, the substituted sulfonamide substituted alcohol is:

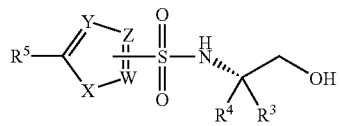

In another embodiment, the compounds prepared are furansulfonamides. Thus, the compounds have a structure in which X is O. In one desirable embodiment, the furansulfonamides are characterized by β-branches in the side chain of a primary alcohol.

In still a further embodiment, the compounds described herein are pyrazole sulfonamides. Thus, the compound has a structure in which X is $NR^7$, W is N and Z and Y are C or $CR^6$, with the proviso that at least one of Y or Z must be C.

In another embodiment, the sulfonamide trifluoroalkyl substituted alcohol is 5-Chloro-N-[(1S)-3,3,3-trifluoro-1-(hydroxymethyl)-2-(trifluoromethyl)propyl]thiophene-2-sulfonamide or 4-Chloro-N-[(1S)-3,3,3-trifluoro-1-(hydroxymethyl)-2-(trifluoromethyl)propyl]benzenesulfonamide.

In one example, $R^3$ is H, $R^4$ is $(CF_3)_2CH$, desirably of S-stereochemistry, $R^5$ is halogen, W is C, X is S, Y is CH, and Z is CH with the sulfonamide attached to C-2 of the thiophene ring.

In another example, $R^3$ is H, $R^4$ is $(CH_2CF_3)_2CH$, $R^5$ is halogen, W is C, X is S, Y is CH, and Z is CH with the sulfonamide attached to C-2 of the thiophene ring.

In yet a further example, $R^3$ is H, $R^4$ is $(F)_2$cycloalkyl, $R^5$ is halogen, W is C, X is S, Y is CH, Z is CH with the sulfonamide attached to C-2 of the thiophene ring.

In still another example, the substituted sulfonamide substituted alcohol is:

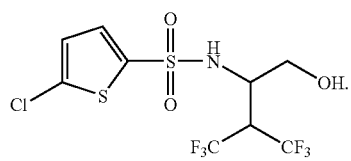

In yet a further example, the substituted sulfonamide substituted alcohol is:

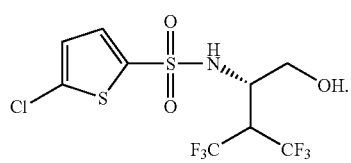

In another embodiment, the sulfonamide substituted alcohol is of the structure:

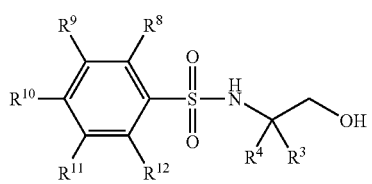

wherein, $R^3$ is selected from among H, lower alkyl and substituted lower alkyl; $R^4$ is selected from among $(CF_3)_n$alkyl, $(CF_3)_n$(substituted alkyl), $(CF_3)_n$alkyl phenyl, $(CF_3)_n$alkyl (substituted phenyl), and $(F)_n$cycloalkyl; n is 1 to 3; $R^8$, $R^9$, $R^{10}$, $R^{11}$, and $R^{12}$ are independently selected from among H, halogen, $C_1$ to $C_6$ alkyl, substituted $C_1$ to $C_6$ alkyl, $C_1$ to $C_6$ alkoxy, substituted $C_1$ to $C_6$ alkoxy, and $NO_2$; or $R^8$ and $R^9$; $R^9$ and $R^{10}$; $R^{11}$ and $R^{12}$; or $R^{10}$ and $R^{11}$ are fused to form (i) a carbon-based saturated ring containing 3 to 8 carbon atoms;

(ii) a carbon-based unsaturated ring containing 3 to 8 carbon atoms; or (iii) a heterocyclic ring containing 1 to 3 heteroatoms selected from among O, N, and S in the backbone of the ring; wherein rings (i) to (iii) are optionally substituted by 1 to 3 substituents including $C_1$ to $C_6$ alkyl or substituted $C_1$ to $C_6$ alkyl.

In one example, the substituted sulfonamide substituted alcohol is:

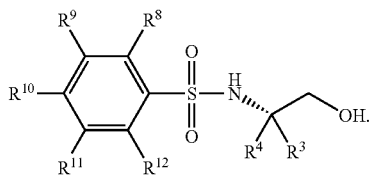

The methods thereby include isolating one diastereomer of an N-protected aminoester by reacting a diastereomeric mixture of N-protected aminoesters with a protic acid to form the corresponding N-protected aminoester salt. The desired diastereomer of the aminoester salt is typically isolated by treating the diastereomeric mixture with a protic acid to form salts of the N-protected aminoesters. The term "protic acid" as used herein refers to any acid that donates a hydrogen atom ($H^+$). A variety of protic acids can be utilized to convert the amino alcohols to the corresponding salt and include, without limitation, hydrochloric acid, sulfuric acid, phosphoric acid, acetic acid, among others. The desired single diastereomeric N-protected aminoester salt precipitates from the solution and is then isolated using techniques in the art such as filtration, decanting, among others. Desirably, the single diastereomeric N-protected aminoester salt is isolated using filtration. The N-protected aminoester salt can then be utilized without further purification or can be purified using techniques known to those of skill in the art.

In one embodiment, the N-protected aminoester salt is of the structure:

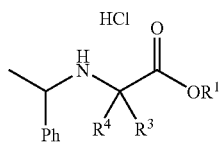

wherein, $R^1$ is alkyl or benzyl; $R^3$ is selected from among hydrogen, lower alkyl and substituted lower alkyl; $R^4$ is selected from among $(CF_3)_n$alkyl, $(CF_3)_n$(substituted alkyl), $(CF_3)_n$alkylphenyl, $(CF_3)_n$alkyl(substituted phenyl), and $(F)_n$cycloalkyl; and n is 1 to 3.

In another embodiment, the N-protected aminoester salt is:

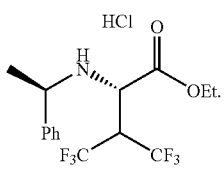

The N-protected aminoester salt is then treated with a base to form the corresponding N-protected aminoester of the single diastereomer. The term based as used herein refers to a chemical compound that is capable of accepting protons. Therefore, the term base includes, without limitation, hydroxides such as potassium, lithium or sodium hydroxide, alkoxides, hydrides, amines, among others and including those described in US Patent Application Publication No. US-2005/0272932, which is hereby incorporated by reference.

The N-protected aminoester is then reduced to the N-protected amino alcohol by adding the N-protected aminoester to DIBAL-H as described above. The reduction is then quenched with a protic solvent as described above to form the N-protected amino alcohol.

The N-protected amino alcohol is then converted to the corresponding N-protected amino alcohol salt by reacting the N-protected amino alcohol with a protic acid as described above.

The N-protected amino alcohol salt is then hydrogenated to form the unprotected amino alcohol salt. One of skill in the art would readily be able to select a suitable hydrogenating agent for use in the hydrogenation. Desirably, hydrogen is utilized in the presence of a catalyst. Catalysts that are useful in the hydrogenation include those recited in Larock et al. cited above, which is hereby incorporated by reference. Desirably, the hydrogenation is performed using Pd/C.

The unprotected amino alcohol salt is then sulfonylated using a sulfonyl chloride to form a sulfonamide substituted alcohol. In one embodiment, the sulfonyl chloride is of the structure:

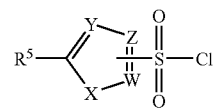

wherein, $R^5$ is selected from among H, halogen, and $CF_3$; W, Y and Z are independently selected from among C, $CR^6$ and N, wherein at least one of W, Y or Z is C; X is selected from among O, S, $SO_2$, and $NR^7$; $R^6$ is selected from among H, halogen, $C_1$ to $C_6$ alkyl, and substituted $C_1$ to $C_6$ alkyl; $R^7$ is selected from among H, $C_1$ to $C_6$ alkyl, and $C_3$ to $C_8$ cycloalkyl.

In another embodiment, the sulfonyl chloride is:

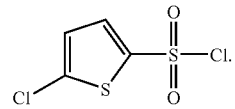

In still a further embodiment, the sulfonyl chloride is of the structure:

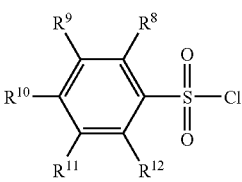

wherein, $R^8$, $R^9$, $R^{10}$, $R^{11}$, and $R^{12}$ are independently selected from among H, halogen, $C_1$ to $C_6$ alkyl, substituted $C_1$ to $C_6$ alkyl, $C_1$ to $C_6$ alkoxy, substituted $C_1$ to $C_6$ alkoxy, and $NO_2$;

or $R^8$ and $R^9$; $R^9$ and $R^{10}$; $R^{11}$ and $R^{12}$; or $R^{10}$ and $R^{11}$ are fused to form: (i) a carbon-based saturated ring containing 3 to 8 carbon atoms; (ii) a carbon-based unsaturated ring containing 3 to 8 carbon atoms; or (iii) a heterocyclic ring containing 1 to 3 heteroatoms selected from among 0, N, and S in the backbone of the ring; wherein rings (i) to (iii) are optionally substituted by 1 to 3 substituents including $C_1$ to $C_6$ alkyl or substituted $C_1$ to $C_6$ alkyl.

Desirably, the sulfonylation is performed in the absence of protection and deprotection steps. More desirably, the sulfonylation is performed in the absence of any silylation or desilylation steps as described in US Patent Application Publication No. US-2004/0198778 A1, which is hereby incorporated by reference.

Typically, the sulfonylation is performed using a base/solvent system including 4-methyl morpholine/isopropyl acetate, Hünig's base/tetrahydrofuran, 4-methyl morpholine/acetonitrile, 4-methyl morpholine/propionitrile, and 4-methyl morpholine/toluene using the procedure described in U.S. Provisional Patent Application No. 60/774, 300, which is hereby incorporated by reference.

The sulfonamide substituted alcohol is then optionally purified using techniques known to those of skill in the art. Desirably, the purification is performed in the absence of chromatography, including the use of silica gel chromatography.

The compounds may contain one or more asymmetric carbon atoms and some of the compounds may contain one or more asymmetric (chiral) centers and may thus give rise to optical isomers and diastereomers. While shown without respect to stereochemistry, when the compounds contain one or more chiral centers, at least the chiral center of the β-amino alcohol is of S-stereochemistry. Desirably, the chiral centers include the carbon atom to which the N-atom, $R^3$, and $R^4$ are attached (the α-carbon atom). More desirably, the α-carbon atom is chiral. Most desirably, the α-carbon atom is chiral and is of S-stereochemistry. Thus, the compounds include such optical isomers and diastereomers; as well as the racemic and resolved, enantiomerically pure stereoisomers; as well as other mixtures of the R and S stereoisomers, and pharmaceutically acceptable salts, hydrates, and prodrugs thereof.

The term "alkyl" is used herein to refer to both straight- and branched-chain saturated aliphatic hydrocarbon groups having one to ten carbon atoms (e.g., $C_1$, $C_2$, $C_3$, $C_4$, $C_5$, $C_6$, $C_7$, $C_8$, $C_9$, or $C_{10}$), such as one to eight carbon atoms (e.g., $C_1$, $C_2$, $C_3$, $C_4$, $C_5$, $C_6$, $C_7$, or $C_8$), one to six carbon atoms (e.g., $C_1$, $C_2$, $C_3$, $C_4$, $C_5$, or $C_6$), or one to four carbon atoms (e.g., $C_1$, $C_2$, $C_3$, or $C_4$). The term "lower alkyl" refers to straight- and branched-chain saturated aliphatic hydrocarbon groups having one to six carbon atoms (e.g., $C_1$, $C_2$, $C_3$, $C_4$, $C_5$, or $C_6$), desirably one to four carbon atoms (e.g., $C_1$, $C_2$, $C_3$, or $C_4$). The term "alkenyl" refers to both straight- and branched-chain alkyl groups with at least one carbon-carbon double bond and two to eight carbon atoms (e.g., $C_2$, $C_3$, $C_4$, $C_5$, $C_6$, $C_7$, or $C_8$), two to six carbon atoms (e.g., $C_2$, $C_3$, $C_4$, $C_5$, or $C_6$), or two to four carbon atoms (e.g., $C_2$, $C_3$, or $C_4$). The term "alkynyl" refers to both straight- and branched-chain alkyl groups with at least one carbon-carbon triple bond and two to eight carbon atoms (e.g., $C_2$, $C_3$, $C_4$, $C_5$, $C_6$, $C_7$, or $C_8$), two to six carbon atoms (e.g., $C_2$, $C_3$, $C_4$, $C_5$, or $C_6$), or two to four carbon atoms (e.g., $C_2$, $C_3$, or $C_4$).

The terms "substituted alkyl", "substituted alkenyl", and "substituted alkynyl" refer to alkyl, alkenyl, and alkynyl groups as just described having from one to three substituents including halogen, CN, OH, $NO_2$, amino, aryl, substituted aryl, heterocyclic, substituted heterocyclic, heteroaryl, substituted heteroaryl, alkoxy, substituted alkoxy, aryloxy, substituted aryloxy, alkylcarbonyl, alkylcarboxy, alkylamino, and arylthio. These substituents may be attached to any carbon of an alkyl, alkenyl, or alkynyl group provided that the attachment constitutes a stable chemical moiety.

The term "cycloalkyl" is used herein to describe a carbon-based saturated ring having more than 3 carbon-atoms and which forms a stable ring. The term cycloalkyl can include groups where two or more cycloalkyl groups have been fused to form a stable multicyclic ring. Desirably, cycloalkyl refers to a ring having about 4 to about 9 carbon atoms, and more desirably about 6 carbon atoms.

The term "substituted cycloalkyl" is used herein to refer to a cycloalkyl group as just described and having from one to five substituents including, without limitation, halogen, CN, OH, $NO_2$, amino, alkyl, substituted alkyl, alkenyl, substituted alkenyl, alkynyl, alkoxy, aryloxy, substituted alkyloxy, alkylcarbonyl, alkylcarboxy, alkylamino, substituted alkylamino, arylthio, heterocyclic, substituted heterocyclic, heteroaryl, substituted heteroaryl, aminoalkyl, and substituted aminoalkyl.

The term "aryl" is used herein to refer to a carbocyclic aromatic system, which may be a single ring, or multiple aromatic rings fused or linked together as such that at least one part of the fused or linked rings forms the conjugated aromatic system. The aryl groups include, but are not limited to, phenyl, naphthyl, biphenyl, anthryl, tetrahydronaphthyl, phenanthryl, and indane. Desirably, aryl refers to a carbocyclic aromatic system having about 6 to about 14 carbon atoms.

The term "substituted aryl" refers to aryl as just defined having one to four substituents including halogen, CN, OH, $NO_2$, amino, alkyl, cycloalkyl, alkenyl, alkynyl, alkoxy, aryloxy, substituted alkyloxy, alkylcarbonyl, alkylcarboxy, alkylamino, and arylthio.

The term "heterocycle" or "heterocyclic" as used herein can be used interchangeably to refer to a stable, saturated or partially unsaturated 3- to 9-membered monocyclic or multicyclic heterocyclic ring. The heterocyclic ring has in its backbone carbon atoms and one or more heteroatoms including nitrogen, oxygen, and sulfur atoms. In one embodiment, the heterocyclic ring contains 1 to about 4 heteroatoms in the backbone of the ring. When the heterocyclic ring contains nitrogen or sulfur atoms in the backbone of the ring, the nitrogen or sulfur atoms can be oxidized. The term "heterocycle" or "heterocyclic" also refers to multicyclic rings in which a heterocyclic ring is fused to an aryl ring of about 6 to about 14 carbon atoms. The heterocyclic ring can be attached to the aryl ring through a heteroatom or carbon atom provided the resultant heterocyclic ring structure is chemically stable. In one embodiment, the heterocyclic ring includes multicyclic systems having 1 to 5 rings.

A variety of heterocyclic groups are known in the art and include, without limitation, oxygen-containing rings, nitrogen-containing rings, sulfur-containing rings, mixed heteroatom-containing rings, fused heteroatom containing rings, and combinations thereof. Examples of heterocyclic groups include, without limitation, tetrahydrofuranyl, piperidinyl, 2-oxopiperidinyl, pyrrolidinyl, morpholinyl, thiamorpholinyl, thiamorpholinyl sulfoxide, pyranyl, pyronyl, dioxinyl, piperazinyl, dithiolyl, oxathiolyl, dioxazolyl, oxathiazolyl, oxazinyl, oxathiazinyl, benzopyranyl, benzoxazinyl and xanthenyl.

The term "heteroaryl" as used herein refers to a stable, aromatic 5- to 14-membered monocyclic or multicyclic heteroatom-containing ring. The heteroaryl ring has in its backbone carbon atoms and one or more heteroatoms including nitrogen, oxygen, and sulfur atoms. In one embodiment, the heteroaryl ring contains 1 to about 4 heteroatoms in the backbone of the ring. When the heteroaryl ring contains nitrogen or sulfur atoms in the backbone of the ring, the nitrogen or sulfur atoms can be oxidized. The term "heteroaryl" also refers to multicyclic rings in which a heteroaryl ring is fused to an aryl ring. The heteroaryl ring can be attached to the aryl ring through a heteroatom or carbon atom provided the resultant heterocyclic ring structure is chemically stable. In one embodiment, the heteroaryl ring includes multicyclic systems having 1 to 5 rings.

A variety of heteroaryl groups are known in the art and include, without limitation, oxygen-containing rings, nitrogen-containing rings, sulfur-containing rings, mixed heteroatom-containing rings, fused heteroatom containing rings, and combinations thereof. Examples of heteroaryl groups include, without limitation, furyl, pyrrolyl, pyrazolyl, imidazolyl, triazolyl, pyridyl, pyridazinyl, pyrimidinyl, pyrazinyl, triazinyl, azepinyl, thienyl, dithiolyl, oxathiolyl, oxazolyl, thiazolyl, oxadiazolyl, oxatriazolyl, oxepinyl, thiepinyl, diazepinyl, benzofuranyl, thionapthene, indolyl, benzazolyl, purindinyl, pyranopyrrolyl, isoindazolyl, indoxazinyl, benzoxazolyl, quinolinyl, isoquinolinyl, benzodiazonyl, napthylridinyl, benzothienyl, pyridopyridinyl, acridinyl, carbazolyl, and purinyl rings.

The term "substituted heterocycle" and "substituted heteroaryl" as used herein refers to a heterocyclic or heteroaryl group having one or more substituents including halogen, CN, OH, $NO_2$, amino, alkyl, cycloalkyl, alkenyl, alkynyl, $C_1$ to $C_3$ perfluoroalkyl, $C_1$ to $C_3$ perfluoroalkoxy, alkoxy, aryloxy, alkyloxy including —O—($C_1$ to $C_{10}$ alkyl) or —O—($C_1$ to $C_{10}$ substituted alkyl), alkylcarbonyl including —CO—($C_1$ to $C_{10}$ alkyl) or —CO—($C_1$ to $C_{10}$ substituted alkyl), alkylcarboxy including —COO—($C_1$ to $C_{10}$ alkyl) or —COO—($C_1$ to $C_{10}$ substituted alkyl), —C($NH_2$)=N—OH, , —$SO_2$—($C_1$ to $C_{10}$ alkyl), —$SO_2$—($C_1$ to $C_{10}$ substituted alkyl), —O—$CH_2$-aryl, alkylamino, arylthio, aryl, substituted aryl, heteroaryl, or substituted heteroaryl which groups may be optionally substituted. A substituted heterocycle or heteroaryl group may have 1, 2, 3, or 4 substituents.

The term "alkoxy" is used herein to refer to the OR group, where R is alkyl or substituted alkyl. The term "lower alkoxy" refers alkoxy groups having one to six carbon atoms.

The term "aryloxy" is used herein to refer to the OR group, where R is aryl or substituted aryl.

The term "arylthio" is used herein to refer to the SR group, where R is aryl or substituted aryl.

The term "alkylcarbonyl" is used herein to refer to the RCO group, where R is alkyl or substituted alkyl.

The term "alkylcarboxy" is used herein to refer to the COOR group, where R is alkyl or substituted alkyl.

The term "aminoalkyl" refers to both secondary and tertiary amines wherein the alkyl or substituted alkyl groups, containing one to eight carbon atoms, may be either the same or different, and the point of attachment is on the nitrogen atom.

The term "halogen" refers to Cl, Br, F, or I.

Pharmaceutically acceptable salts can be formed from organic and inorganic acids including, e.g., acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids. Salts may also be formed from inorganic bases, desirably alkali metal salts including, e.g., sodium, lithium, or potassium, and organic bases, such as ammonium salts, mono-, di-, and trimethylammonium, mono-, di- and triethylammonium, mono-, di- and tripropylammonium (iso and normal), ethyl-dimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butyl piperidinium, 2-methylpiperidinium, 1-ethyl-2-methylpiperidinium, mono-, di- and triethanolammonium, ethyl diethanolammonium, n-butylmonoethanolammonium, tris(hydroxymethyl)methylammonium, phenylmonoethanolammonium, and the like.

Physiologically acceptable alkali salts and alkaline earth metal salts can include, without limitation, sodium, potassium, calcium and magnesium salts in the form of esters, and carbamates.

These salts, as well as other compounds, can be in the form of esters, carbamates and other conventional "pro-drug" forms, which, when administered in such form, convert to the active moiety in vivo. In one embodiment, the prodrugs are esters. In another embodiment, the prodrugs are carbamates. See, e.g., B. Testa and J. Caldwell, "Prodrugs Revisited: The "Ad Hoc" Approach as a Complement to Ligand Design", Medicinal Research Reviews, 16(3):233-241, ed., John Wiley & Sons (1996).

In one example, a method is provided for preparing a sulfonamide substituted alcohol, including isolating one diastereomer of a N-protected aminoester by reacting a mixture of diastereomers of a N-protected aminoester with a protic acid to form a N-protected aminoester salt; neutralizing the N-protected aminoester salt with a base to form a N-protected aminoester; reducing the N-protected aminoester by adding the N-protected aminoester to a reducing agent at −60° C. to about −10° C.; quenching the reduction with a protic solvent; reacting the N-protected amino alcohol with a protic acid to form a N-protected amino alcohol salt; hydrogenating the N-protected amino alcohol salt to form an unprotected amino alcohol salt; and sulfonylating the unprotected amino alcohol with a sulfonyl chloride in the presence of a base/solvent system. See, Scheme 3.

Scheme 3

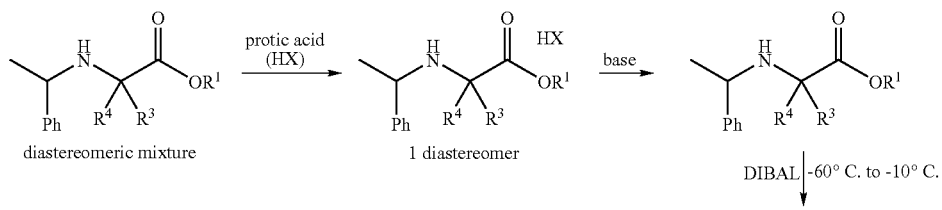

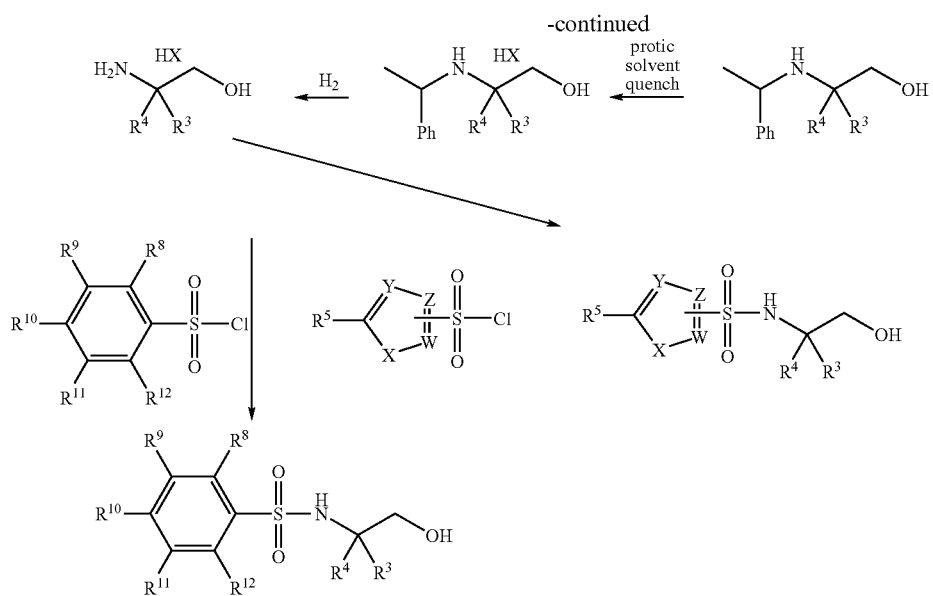

In another example, a method is provided for preparing a sulfonamide substituted alcohol, including isolating one diastereomer of a N-protected aminoester by reacting a mixture of diastereomers of a N-protected aminoester with a protic acid to form a N-protected aminoester salt; neutralizing the N-protected aminoester salt with a base to form a N-protected aminoester; reducing the N-protected aminoester by adding the N-protected aminoester to diisobutylaluminum hydride at −60° C. to about −10° C.; quenching the reduction with a protic solvent; reacting the N-protected amino alcohol with a protic acid to form a N-protected amino alcohol salt; hydrogenating the N-protected amino alcohol salt to form an unprotected amino alcohol salt; and sulfonylating the unprotected amino alcohol with a sulfonyl chloride in the presence of a base/solvent system.

In a further example, a method is provided for preparing a sulfonamide substituted alcohol, including isolating one diastereomer of a N-protected aminoester by reacting a mixture of diastereomers of a N-protected aminoester with a protic acid to form a N-protected aminoester salt; neutralizing the N-protected aminoester salt with a base to form a N-protected aminoester; reducing the N-protected aminoester by adding the N-protected aminoester to diisobutylaluminum hydride at −60° C. to about −10° C.; quenching the reduction with a protic solvent; reacting the N-protected amino alcohol with a protic acid to form a N-protected amino alcohol salt; hydrogenating the N-protected amino alcohol salt to form an unprotected amino alcohol salt; and sulfonylating the unprotected amino alcohol with a sulfonyl chloride in the presence of a base/solvent system selected from among 4-methyl morpholine/isopropyl acetate, Hünig's base/tetrahydrofuran, 4-methyl morpholine/acetonitrile, 4-methyl morpholine/propionitrile, and 4-methyl morpholine/toluene.

In yet another example, a method is provided for preparing a sulfonamide substituted alcohol, including isolating one diastereomer of a N-protected aminoester by reacting a mixture of diastereomers of a N-protected aminoester with a protic acid to form a N-protected aminoester salt; neutralizing the N-protected aminoester salt with a base to form a N-protected aminoester; reducing the N-protected aminoester by adding the N-protected aminoester to diisobutylaluminum hydride at −60° C. to about −10° C.; quenching the reduction with a protic solvent; reacting the N-protected amino alcohol with a protic acid to form a N-protected amino alcohol salt; hydrogenating the N-protected amino alcohol salt to form an unprotected amino alcohol salt; and sulfonylating the unprotected amino alcohol with a sulfonyl chloride in the presence of a base/solvent system, wherein the sulfonylation is performed in the absence of protection and deprotection steps.

In still a further example, a method is provided for preparing a sulfonamide substituted alcohol, including isolating one diastereomer of a N-protected aminoester by reacting a mixture of diastereomers of a N-protected aminoester with a protic acid to form a N-protected aminoester salt; neutralizing the N-protected aminoester salt with a base to form a N-protected aminoester; reducing the N-protected aminoester by adding the N-protected aminoester to diisobutylaluminum hydride at −60° C. to about −10° C.; quenching the reduction with a protic solvent; reacting the N-protected amino alcohol with a protic acid to form a N-protected amino alcohol salt; hydrogenating the N-protected amino alcohol salt to form an unprotected amino alcohol salt; sulfonylating the unprotected amino alcohol with a sulfonyl chloride in the presence of a base/solvent system; and purifying the sulfonamide substituted alcohol, wherein the purification is performed in the absence of silica gel.

The following examples are illustrative only and are not intended to be a limitation on the present invention.

EXAMPLES

Example 1

Preparation of 4,4,4-Trifluoro-2-(1-Phenethylamino)-3-Trifluoromethylbutan-1-ol

A solution of 50% NaOH (24 g, 0.302 mol) in water (80 mL) was added to a suspension of ethyl 4,4,4,4',4',4'-hexafluoro-N-[(1R)-1-phenylethyl]-L-valinate hydrochloride salt aminoester (100 g, 0.254 mol) in water (278 mL) and toluene (1.01 L). The mixture was stirred for 30 minutes and then the two phases were separated. The toluene layer was washed with water (2×195 mL) and the water was removed by azeotroping. The toluene solution was distilled under atmospheric pressure until the vapor temperature reached about 108-110° C., whereby about 600 mL of toluene remained in the flask.

A solution of DIBAL-H in toluene (1.5 N, 518 mL, 0.78 mol) was cooled to −10° C. and then the aminoester toluene solution (about 600 mL) was added over about 90 minutes while keeping the reaction mixture at about −8 to −11° C. The mixture was then stirred for about 10 minutes. EtOH (29 mL, 0.5 mol) was then added over 10 minutes, while keeping the reaction temperature below 25° C.

A solution of concentrated HCl (93 g) in water (130 mL) was heated to 35-40° C. The reaction mixture was then added to this heated HCl solution over 60 to 90 minutes while maintaining the temperature below 45° C. This mixture was then stirred at 40-45° C. for 30 minutes. The two layers were separated and the organic layer was washed with 15% NaCl (700 mL). The organic layer solution was then cooled to −5° C. and then concentrated HCl (32 g, 0.33 mol) was added over 15 minutes. This mixture was then stirred for 6 hours. The salt product from the previous step was then isolated by filtration, washed with toluene (2×200 mL) and dried in a vacuum oven to give 81 g (90%) of the final product as an off-white solid. 98.9 area % HPLC purity, 98.5% strength.

Example 2

Preparation of 5-Chloro-N-[(1S)-3,3,3-trifluoro-1-(hydroxymethyl)-2-(trifluoro-methyl)propyl]thiophene-2-sulfonamide 4-methyl morpholine (2.7 mL, 24.6 mmol) was added to a suspension of (2S)-2-amino-4,4,4-tri-fluoro-3-(trifluoromethyl)butan-1-ol (2 g, 8.1 mmol) in isopropyl acetate (10 mL). The mixture was stirred at about 20-25° C. for about 5-10 minutes and then 5-chlorothiophene-2-sulfonyl chloride (2.0 g, 9.2 mmol) was added. The reaction mixture was stirred at 20-25° C. for 6-18 hours. Water (10 mL) was then added to the reaction mixture, whereby the solids dissolved. The two layers were then separated and the organic layer was washed with a solution of 10% NaHCO₃ (10 mL) and 10% NaCl (10 mL). Heptane (10 mL) was added to the isopropyl acetate layer (about 10 mL). The mixture was then distilled down to about half of its original volume under atmospheric distillation. While the solution remained at about 80-90° C., heptane (10 mL) was added over 5-10 minutes, during which time solids formed. After the addition of heptane, the mixture was cooled to 20-25° C., stirred for about 1-2 hours, and then further cooled to about 5-10° C. for 1 hour. The solid was then collected by filtration, washed with heptane (5 mL), and oven-dried to give 2.15 g (67%) of the product as an off-white solid. 98 area% HPLC purity and >99% chiral purity by HPLC.

All publications cited in this specification are incorporated herein by reference. While the invention has been described with reference to particular embodiments, it will be appreciated that modifications can be made without departing from the spirit of the invention. Such modifications are intended to fall within the scope of the appended claims.

What is claimed is:

1. A method for preparing an amino alcohol, or salt thereof, from an aminoester of the structure:

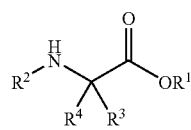

wherein:

R¹ is alkyl or benzyl;
R² is a protecting group;
R³ is hydrogen;
R⁴ is (CF₃)ₙalkyl;
n is 1 to 3;

said method comprising reducing said aminoester by adding said aminoester to a hydride reducing agent in a solvent selected from the group consisting of toluene, tetrahydrofuran, hexanes, heptane, dichloromethane, and cyclohexane at about −60° to about −10° C.

2. The method according to claim 1, wherein said aminoester is of the structure:

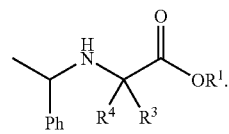

3. The method according to claim 2, wherein said aminoester is:

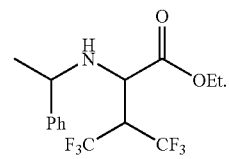

4. The method according to claim 1, wherein said amino alcohol is of the structure:

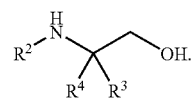

5. The method according to claim 4, wherein said amino alcohol is:

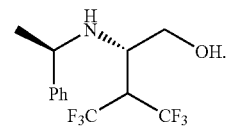

6. The method according to claim 1, wherein said amino alcohol salt is of the structure:

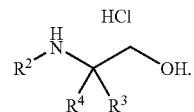

7. The method according to claim 6, wherein said amino alcohol salt is:

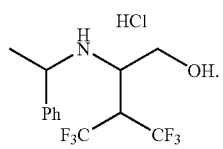

8. The method according to claim 1, wherein said hydride reducing agent is diisobutylaluminum hydride.

9. The method according to claim 1, further comprising quenching the reduction with a protic solvent.

10. The method according to claim 9, wherein said protic solvent is hydrochloric acid, acetic acid, or ethanol.

11. The method according to claim 1, wherein the reduction is performed at about −20 to about −10° C.

12. The method according to claim 1, wherein said amino alcohol is prepared in a yield of about 90 to about 95%.

13. A method for preparing an amino alcohol of the structure:

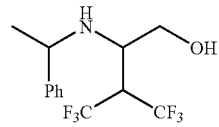

wherein said method comprises reducing an aminoester of the following structure by adding said aminoester to diisobutylaluminum hydride at about −60° to about −10° C.

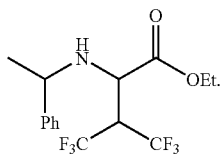

14. A method for preparing a sulfonamide substituted alcohol, or a pharmaceutically acceptable salt thereof, said method comprising:
(a) isolating one diastereomer of a N-protected aminoester by reacting a mixture of diastereomers of a N-protected aminoester with a protic acid to form a N-protected aminoester salt;
(b) neutralizing said N-protected aminoester salt with a base to form an N-protected aminoester of the following structure:

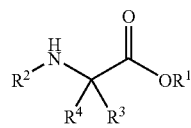

wherein:
R$^1$ is alkyl or benzyl;
R$^2$ is protecting group;
R$^3$ is hydrogen;
R$^4$ is (CF$_3$)$_n$alkyl;
n is 1 to 3;

(c) reducing said N-protected aminoester by adding said N-protected aminoester to diisobutylaluminum hydride in a solvent selected from the group consisting of toluene, tetrahydrofuran, hexanes, heptane, dichloromethane, and cyclohexane at −60° C. to about −10° C.;
(d) quenching the reaction of step (c) with a protic solvent;
(e) reacting the N-protected amino alcohol of step (d) with a protic acid to form a N-protected amino alcohol salt;
(f) hydrogenating said N-protected amino alcohol salt to form an unprotected amino alcohol salt of the following structure:

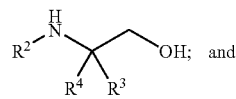

(g) sulfonylating said unprotected amino alcohol with a sulfonyl chloride in the presence of a base/solvent system.

15. The method according to claim 14, wherein said base/solvent system is selected from the group consisting of 4-methyl morpholine/isopropyl acetate, Hünig's base/tetrahydrofuran, 4-methyl morpholine/acetonitrile, 4-methyl morpholine/propionitrile, and 4-methyl morpholine/toluene.

16. The method according to claim 14, wherein said sulfonylation is performed in the absence of protection and deprotection steps.

17. The method according to claim 14, further comprising:
(h) purifying said sulfonamide substituted alcohol,
wherein said purification is performed in the absence of silica gel.

18. The method according to claim 14, wherein said sulfonamide substituted alcohol, or a pharmaceutically acceptable salt thereof, is of the structure:

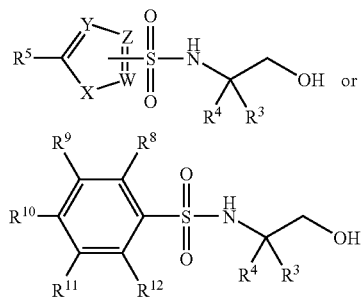

wherein:
R$^3$ is H;
R$^4$ is (CF$_3$)$_n$alkyl;
n is 1 to 3;
R$^5$ is selected from the group consisting of H, halogen, CF$_3$, diene fused to Y when Y is C, and substituted diene fused to Y when Y is C;
W, Y and Z are independently selected from the group consisting of C, CR$^6$ and N, wherein at least one of W, Y or Z is C;
X is selected from the group consisting of O, S, SO$_2$, and NR$^7$;
R$^6$ is selected from the group consisting of H, halogen, C$_1$ to C$_6$ alkyl, and substituted C$_1$ to C$_6$ alkyl;
R$^7$ is selected from the group consisting of H, C$_1$ to C$_6$ alkyl, and C$_3$ to C$_8$ cycloalkyl;

$R^8$, $R^9$, $R^{10}$, $R^{11}$, and $R^{12}$ are independently selected from the group consisting of H, halogen, $C_1$ to $C_6$ alkyl, substituted $C_1$ to $C_6$ alkyl, $C_1$ to $C_6$ alkoxy, substituted $C_1$ to $C_6$ alkoxy, and $NO_2$; or $R^8$ and $R^9$; $R^9$ and $R^{10}$; $R^{11}$ and $R^{12}$; or $R^{10}$ and $R^{11}$ are fused to form:
 (i) a carbon-based saturated ring containing 3 to 8 carbon atoms;
 (ii) a carbon-based unsaturated ring containing 3 to 8 carbon atoms; or
 (iii) a heterocyclic ring containing 1 to 3 heteroatoms selected from the group consisting of O, N, and S in the backbone of said ring;
 wherein rings (i) to (iii) are optionally substituted by 1 to 3 substituents comprising $C_1$ to $C_6$ alkyl or substituted $C_1$ to $C_6$ alkyl;

or a pharmaceutically acceptable salt thereof.

19. The method according to claim 18, wherein said sulfonamide substituted alcohol, or a pharmaceutically acceptable salt thereof, is:

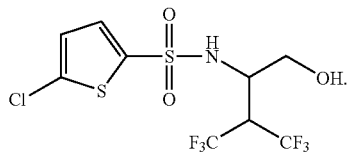

20. The method according to claim 19, wherein said sulfonamide substituted alcohol, or a pharmaceutically acceptable salt thereof, is:

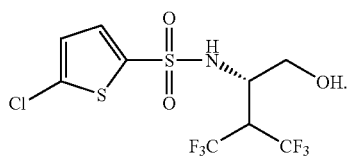

21. The method according to claim 14, wherein the hydrogenation is performed with a catalyst.

22. The method according to claim 14, wherein said unprotected amino alcohol salt is of the structure:

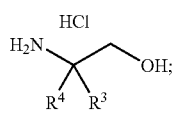

wherein:
 $R^3$ is hydrogen;
 $R^4$ is $(CF_3)_n$alkyl;
 n is 1 to 3.

23. The method according to claim 22, wherein said unprotected amino alcohol salt is:

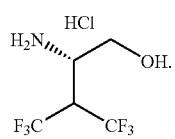

24. The method according to claim 14, wherein said sulfonyl chloride is of the structure:

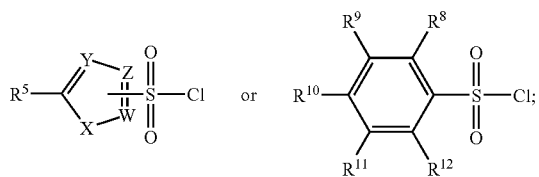

wherein:
 $R^5$ is selected from the group consisting of H, halogen, and $CF_3$;
 W, Y and Z are independently selected from the group consisting of C, $CR^6$ and N, wherein at least one of W, Y or Z is C;
 X is selected from the group consisting of O, S, $SO_2$, and $NR^7$;
 $R^6$ is selected from the group consisting of H, halogen, $C_1$ to $C_6$ alkyl, and substituted $C_1$ to $C_6$ alkyl;
 $R^7$ is selected from the group consisting of H, $C_1$ to $C_6$ alkyl, and $C_3$ to $C_8$ cycloalkyl;
 $R^8$, $R^9$, $R^{10}$, $R^{11}$, and $R^{12}$ are independently selected from the group consisting of H, halogen, $C_1$ to $C_6$ alkyl, substituted $C_1$ to $C_6$ alkyl, $C_1$ to $C_6$ alkoxy, substituted $C_1$ to $C_6$ alkoxy, and $NO_2$; or
 $R^8$ and $R^9$; $R^9$ and $R^{10}$; $R^{11}$ and $R^{12}$; or $R^{10}$ and $R^{11}$ are fused to form:
  (i) a carbon-based saturated ring containing 3 to 8 carbon atoms;
  (ii) a carbon-based unsaturated ring containing 3 to 8 carbon atoms; or
  (iii) a heterocyclic ring containing 1 to 3 heteroatoms selected from the group consisting of O, N, and S in the backbone of said ring;
  wherein rings (i) to (iii) are optionally substituted by 1 to 3 substituents comprising $C_1$ to $C_6$ alkyl or substituted $C_1$ to $C_6$ alkyl.

25. The method according to claim 24, wherein said sulfonyl chloride is:

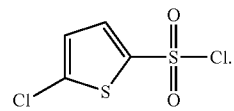

26. The method according to claim 14, wherein said N-protected aminoester is of the structure:

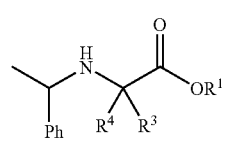

wherein:
 $R^1$ is alkyl or benzyl;
 $R^4$ is $(CF_3)_n$alkyl;
 $R^3$ is hydrogen;
 n is 1 to 3.

27. The method according to claim 26, wherein said N-protected aminoester is:

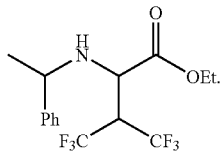

28. The method according to claim 14, wherein said N-protected aminoester salt is of the structure:

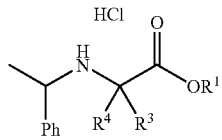

wherein:
- $R^1$ is alkyl or benzyl;
- $R^3$ is hydrogen;
- $R^4$ is $(CF_3)_n$alkyl;
- n is 1 to 3.

29. The method according to claim 28, wherein said N-protected aminoester salt is:

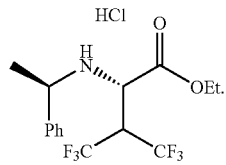

30. The method according to claim 14, wherein said N-protected amino alcohol salt is of the structure:

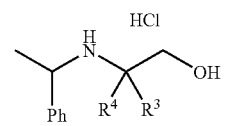

wherein:
- $R^3$ is hydrogen;
- $R^4$ is $(CF_3)_n$alkyl;
- n is 1 to 3.

31. The method according to claim 30, wherein said N-protected amino alcohol hydrochloride salt is:

* * * * *